(12) United States Patent
Mason et al.

(10) Patent No.: US 8,465,434 B2
(45) Date of Patent: Jun. 18, 2013

(54) METHOD AND SYSTEM FOR DETECTION OF RESPIRATORY VARIATION IN PLETHYSMOGRAPHIC OXIMETRY

(75) Inventors: Gregory R. Mason, Manhattan Beach, CA (US); John M. Criley, Palos Verdes, CA (US)

(73) Assignee: Los Angeles Biomedical Research Institute at Harbor-UCLA Medical Center, Torrance, CA (US)

( * ) Notice: Subject to any disclaimer, the term of this patent is extended or adjusted under 35 U.S.C. 154(b) by 0 days.

(21) Appl. No.: 13/404,265

(22) Filed: Feb. 24, 2012

(65) Prior Publication Data
US 2012/0172688 A1 Jul. 5, 2012

Related U.S. Application Data

(62) Division of application No. 12/315,813, filed on Dec. 5, 2008, now Pat. No. 8,128,569.

(60) Provisional application No. 60/992,973, filed on Dec. 6, 2007.

(51) Int. Cl.
*A61B 5/08* (2006.01)

(52) U.S. Cl.
USPC .......................................................... 600/484

(58) Field of Classification Search
USPC .......................................................... 600/484
See application file for complete search history.

(56) References Cited

U.S. PATENT DOCUMENTS

| | | | |
|---|---|---|---|
| 5,144,956 A | 9/1992 | Souma | |
| 5,632,272 A | 5/1997 | Diab et al. | |
| 6,002,952 A | 12/1999 | Diab et al. | |
| 6,129,675 A | 10/2000 | Jay | |
| 6,157,850 A | 12/2000 | Diab et al. | |
| 6,263,222 B1 | 7/2001 | Diab et al. | |
| 6,325,761 B1 | 12/2001 | Jay | |
| 6,334,065 B1 | 12/2001 | Al-Ali et al. | |
| 6,650,917 B2 | 11/2003 | Diab et al. | |
| 6,699,194 B1 | 3/2004 | Diab et al. | |
| 6,745,060 B2 | 6/2004 | Diab et al. | |
| 6,770,028 B1 | 8/2004 | Ali et al. | |

(Continued)

OTHER PUBLICATIONS

American Thoracic Society, "Standards for the Diagnosis and Care of Patients with Chronic Obstructive Pulmonary Disease", Am J Respir Crit Care Med, 152, (1995), S77-S121.

(Continued)

*Primary Examiner* — Patricia Mallari
*Assistant Examiner* — Christian Jang
(74) *Attorney, Agent, or Firm* — Blakely Sokoloff Taylor & Zafman LLP

(57) ABSTRACT

A method and system for detection of respiratory variation in pulse oximetry are provided. In one embodiment, the method includes detecting a pattern consistent with a respiratory cycle of a waveform representing cardiac oscillations and identifying an abnormality based on the pattern. A system is further provided including a database and a module. The database to store data representing a physiological condition of a patient over a period of time, wherein the data comprises data corresponding to respiratory activity and data corresponding to cardiac oscillations, wherein the data corresponding to respiratory activity comprises a first waveform and the data corresponding to the cardiac oscillations comprises a second waveform; and a module for detecting a pattern of the second waveform consistent with a cycle of a first waveform and detecting an abnormality in the pattern.

8 Claims, 5 Drawing Sheets

U.S. PATENT DOCUMENTS

| | | | |
|---|---|---|---|
| 6,869,402 | B2 | 3/2005 | Arnold |
| 7,044,917 | B2 | 5/2006 | Arnold |
| 7,215,984 | B2 | 5/2007 | Diab et al. |
| 7,292,883 | B2 | 11/2007 | De Felice et al. |
| 2001/0012917 | A1 | 8/2001 | Inukai et al. |
| 2003/0163054 | A1* | 8/2003 | Dekker .......................... 600/502 |
| 2004/0044276 | A1 | 3/2004 | Arnold |
| 2005/0107712 | A1 | 5/2005 | Arnold |
| 2005/0251056 | A1 | 11/2005 | Gribkov |
| 2006/0253040 | A1 | 11/2006 | Stergiopoulos et al. |
| 2008/0064965 | A1 | 3/2008 | Jay et al. |
| 2008/0269625 | A1 | 10/2008 | Halperin et al. |

OTHER PUBLICATIONS

Arnold, D. H., et al., "Estimation of airway obstruction using oximeter plethysmograph waveform data", Respir. Res., 6(1), (2005), 65.

Bacon, A. K., "Crisis management during anaesthesia: pnuemothorax", Quality and Safety in Health Care, 14(18), (2005), 5 pages.

Barach, P., "Pulsus Paradoxus", Hospital Physician, 1, (Jan. 2000), 49-50.

Barbieri, R., et al., "Model Dependency of Multivariate Autoregressive Spectral Analysis", IEEE Engineering in Medicine and Biology, 16(5), (Sep.-Oct. 1997), 74-85.

Baselli, G., et al., "Spectral Decomposition in Multichannel Recordings Based on Multivariate Parametric Identification", IEEE Transactions on Biomedical Engineering, 44(11), (Nov. 1997), 1092-1101.

Bilchick, K. C., et al., "Paradoxical physical findings described by Kussmaul: pulsus paradoxus and Kussmaul's sign", The Lancet, vol. 359, No. 9321, (Jun. 1, 2002), 1940-1942.

BioSig Project, "BioSig for Octave and Matlab", accessed via Internet: http://biosig.sourceforge.net on Nov. 13, 2005, 1 page.

Brathwaite, Collin E., et al., "Continuous Pulse Oximetry and the Diagnosis of Pulmonary Embolism in Critically III Trauma Patients", The Journal of Trauma, vol. 33, No. 4, (Oct. 1992), 528-531.

Computational Intelligence Group, "The R Project for Statistical Computing", accessed via Internet: http://www.r-project.org on Nov. 13, 2005, 1 page.

Curtiss, Edward I., et al., "Pulsus paradoxus: Definition and relation to the severity of cardiac tamponade", Am Heart J, 115(2), (1988), 391-398.

Duhamel, P., "Implementation of "Split-Radix" FFT Algorithms for Complex, Real, and Real-Symmetric Data", IEEE Transactions on Acoustics, Speech and Signal Processing, 34(2), (Apr. 1986), 285-295.

Fowler, N. O., "Cardiac tamponade: A Clinical or an Echocardiographic Diagnosis?", Circulation, 87(5), (May 1993), 1738-1741.

Fowler, N. O., "Physiology of Cardiac Tamponade and Pulsus Paradoxus, II: physiological, circulatory, and pharmacological responses in cardiac tamponade", Mod Concepts Cardiovasc Disease, vol. 47, No. 12, (Dec. 1978), 115-118.

Frey, B., et al., "Pulse oximetry for assessment of pulsus paradoxus: a clinical study in children", Intensive Care Medicine, 24, (1998), 242-246.

Guberman, B. A., et al., "Cardiac Tamponade in Medical Patients", Circulation, 64(3), (Sep. 1981), 633-640.

Hartert, T. V., et al., "Use of Pulse Oximetry to Recognize Severity of Airflow Obstruction in Obstructive Airway Disease", Chest, 115(2), (Feb. 1999), 475-481.

Hegde, A., et al., "Investigating Spatio-Temporal Synchronizations in Epileptic ECOG", University of Computational NeuroEngineering Laboratory, www.dnel.ufl.edu/files/1098114461.ppt, (Nov. 13, 2005).

Heideman, M. T., et al., "Gauss and the History of the Fast Fourier Transform", IEEE Acoustics, Speech and Signal Processing Magazine, 1, (Oct. 1984), 14-21.

Irizarry, R. A., "Local Regression with Meaningful Parameters", American Statistician, 55, (2001), 72-79.

Jardin, F., et al., "Mechanism of paradoxic pulse in bronchial asthma", Circulation, 66(4), (1982), 887-894.

Kolba, D. P., "A Prime Factor FFT Algorithm Using High-Speed Convolution", IEEE Transactions on Acoustics, Speech and Signal Processing, 25(4), (Aug. 1977), 281-294.

Kussmaul, A., "Ueber schwielige Mediastino-Pericarditis und den paradoxen Puls", Berliner Klinische Wochenschrift, 10, (1873), 433-435, 445-449 and 461-464.

La BioMed, International Search Report and Written Opinion dated Jan. 7, 2010 for PCT/US2009/061930.

La BioMed, International Preliminary Report on Patentability mailed May 5, 2011 for PCT/US2009/061930.

La BioMed, Non-final Office Action mailed Jun. 6, 2011 for U.S. Appl. No. 12/315,813, 13 pages.

Laishley, R. S., et al., "Tension Pneumothorax and Pulse Oximetry", British Journal of Anaesthesia, 66, (1991), 250-252.

Levine, Marc J., et al., "Implications of Echocardiographically Assisted Diagnosis of Pericardial Tamponade in Contemporary Medical Patients: Detection Before Hemodynamic Embarrassment", J Am Coll Cardiol., vol. 17, No. 1, (Jan. 1991), 59-65.

Los Angeles Biomedical Research, Final Office Action mailed Oct. 11, 2011 for U.S. Appl. No. 12/315,813., 8 pages.

McCaig, L. F., "National Hospital Ambulatory Medical Care Survey: 2003 Emergency Department Survey", Advance Data, 358, (May 26, 2005), 38 pages.

Mower, W. R., "Pulse Oximetry as a Fifth Pediatric Vital Sign", Pediatrics, 99, (1997), 681-686.

National Center for Health, Statistics, "Fast Stats from A to Z: Asthma", accessed via Internet: http://www.cdc.gov/nchs/fastats/asthma.htm on Jul. 12, 2005, 2 pages.

National Heart, Blood & Lung, Institute, "Guidelines for the Diagnosis and Management of Asthma", Journal of Allergy and Clinical Immunology, vol. 88, No. 3, Part 2, (Sep. 1991), 496-502.

National Heart, Blood & Lung, Institute, "Practical Guide for the Diagnosis and Management of Asthma", NIH Publication No. 97-4053, 60 pages, (Oct. 1997).

Netlib.com, "Netlib libraries for computational mathematics", Accessed via Internet: http://www.netlib.org/liblist.html on Nov. 13, 2005, 2 pages.

Plummer, M., et al., "Integrated ARMA Time Series Modelling", Lund University Center for Mathematical Sciences, http://www.maths.lth.se/help/R/.R/library/fSeries/html/A1-armaModelling.html, retrieved Jun. 18, 2010, 8 pages.

Rao, Y. N., "A Fast On-line Generalized Eigendecomposition Algorithm for Time Series Segmentation", IEEE Symposium on Adaptive Systems for Signal Proc. Commun. and Controls, Alberta, Canada, (2000), 266-271.

Rayner, J., et al., "Continuous Noninvasive Measurement of Pulsus Paradoxus Complements Medical Decision Making in Assessment of Acute Asthma Severity", Chest, 130(3), (Sep. 2006), 754-765.

Reddy, P. S., et al., "Cardiac Tamponade", Cardiology Clinics, vol. 8, No. 4, (Nov. 1990), 627-637.

Reddy, P. S., et al., "Cardiac Tamponade: Hemodynamic Observations in Man", Circulation, 58(2), (Aug. 1978), 265-272.

Reddy, P. S., et al., "Spectrum of Hemodynamic Changes in Cardiac Tamponade", Am J Cardiol, 66, (Dec. 15, 1990), 1487-1491.

Roy, C. L., et al., "Does This Patient With a Pericardial Effusion Have Cardiac Tamponade?", JAMA, 297(16), (Apr. 25, 2007), 1810-1818.

Salyer, J. W., "Neonatal and Pediatric Pulse Oximetry", Respiratory Care, 48(4), (2003), 386-396.

Shamir, M., et al., "Pulse oximetry plethysmographic waveform during changes in blood volume", British Journal of Anaesthesia, 82(2), (1999), 178-181.

Singh, S., et al., "Right ventricular and right atrial collapse in patients with cardiac tamponade—a combined echocardiographic and hemodynamic study", Circulation, 70(6), (Dec. 1984), 966-971.

Systat Software Corporation, "AutoSignal 1.7", Accessed via Internet: http://www.systat.com/products/AutoSignal on Nov. 12, 2005, 3 pages.

Tamburro, R. F., "Detection of Pulsus Paradoxus Associated with Large Pericardial Effusions in Pediatric Patients by Analysis of the Pulse-Oximetry Waveform", Pediatrics, 109(4), (Apr. 2002), 673-677.

Thong, T., et al., "Nonlinear Reconstruction of Over-Sampled Coarsely Quantized Signals", IEEE 45th Midwest Symposium on Circuits and Systems, Tulsa, Oklahoma, vol. 2, (Aug. 4-7, 2002), 416-417.

Tremper, K. K., "Pulse Oximetry's Final Frontier", Critical Care Medicine, 28(5), (May 2000), 1684-1685.

Van Steenis, H. G., "Time-Frequency Parameters of Heart-Rate Variability", IEEE Engineering in Medicine and Biology, 21(4), (Jul.-Aug. 2002), 46-58.

Varri, A., et al., "Standards for Biomedical Signal Databases", IEEE Engineering in Medicine and Biology, 20(3), (May-Jun. 2001), 33-38.

Winkler, R., et al., Statistics: Probability, Inference, and Decision, 2nd Edition, Holt Reinhart Winston, (1975), 643-655.

Working Group on Blood Pressure, and Heart Rate Variability of T., "Glossary of Terms Used in Time Series Analysis of Cardiovascular Data", Accessed via Internet: http://www.cbi.dongnocchi.it/glossary/Glossary.html on Nov. 13, 2005, 7 pages.

La BioMed Research, Non-Final Office Action dated Sep. 19, 2012 for U.S. Appl. No. 12/604,346.

* cited by examiner

METHOD AND SYSTEM FOR DETECTION OF RESPIRATORY VARIATION IN PLETHYSMOGRAPHIC OXIMETRY

CROSS REFERENCE TO RELATED APPLICATIONS

This is a divisional of co-pending U.S. patent application Ser. No. 12/315,813, filed Dec. 5, 2008, which claims priority from U.S. Provisional Patent Application No. 60/992,973, filed on Dec. 6, 2007.

BACKGROUND

1. Field

A method and system for detection of variations in plethysmographic oximetry.

2. Background

Pulsus paradoxus is a term referring to a systolic arterial pressure and pulse pressure that weakens abnormally during inspiration. It was first recognized in 1873 when an irregularity of the palpable pulse was observed while the heart sounds indicated that the cardiac rhythm was regular. It was found that the "irregularity" of the pulse resulted from a reduction in left ventricular stroke volume leading to an impalpable pulse during inspiration. Pulsus paradoxus may be symptomatic of various abnormalities including pericardial tamponade, worsening asthma, chronic obstructive pulmonary disease, congestive heart failure, pulmonary edema, chronic dyspnea, obstructive sleep apnea and tension pneumothorax. If left undetected, these disorders may result in deterioration or death of critically ill patients. Thus, early detection is essential.

In a healthy individual, arterial and venous blood pressure vary throughout the respiratory cycle. It is not uncommon to see an increase in blood pressure during expiration followed by a decrease in blood pressure during inspiration. Such fluctuations may occur due to the intrathoracic pressure changes generated during breathing. Although the exact physiology behind pulsus paradoxus may vary depending upon the disease it is symptomatic of, the exaggerated pressure decrease may generally be explained by the interrelationship between the changing intrathoracic pressure during the respiratory cycle and the two ventricular chambers of the heart. During inspiration intrathoracic pressure decreases which augments right heart filling, pulmonary vascular compliance, and right ventricular stroke volume while reducing left heart filling and output.

Pulsus paradoxus may be detected by monitoring changes in blood pressure throughout the respiratory cycle. Under normal conditions, an individual may experience a decrease in arterial blood pressure of less than 10 millimeters mercury (mmHg) during inspiration. An abnormality is identified where this pressure decrease exceeds 10 mmHg. Currently there are a variety of techniques available for detecting this pressure decrease during inspiration.

One such technique for detection of pulsus paradoxus requires gradually deflating a sphygmomanometer (blood pressure cuff) while listening for the onset of Korotkoff sounds (sounds resulting from arterial pressure waves passing through the occluding cuff) during normal respiration. The Korotkoff sounds will first be audible during expiration only, and after further deflation of the cuff, during inspiration as well. If the cuff is deflated more than 10 mmHg between detection of intermittent and constant Korotkoff sounds, pulsus paradoxus is said to be present. This method of detection is problematic for a number of reasons, not the least of which is that automated blood pressure monitoring recording is now standard throughout the health care industry and this technique is incapable of detecting respiratory fluctuations in arterial pressure since only one set of systolic and diastolic pressures are recorded. Even when manual sphygmomanometers are available, the operator has to be alerted to the possibility that pulsus paradoxus could be present and know how to perform the test. In addition, blood pressure values are subjective in that they are reliant upon the operator's ability to listen to the sounds while watching the fluctuations of the gauge. The only record is therefore the operators' hand-written description of a highly subjective test.

A second technique used in detecting pulsus paradoxus is by direct monitoring of arterial pressure with an indwelling intra-arterial catheter. This technique is more accurate than sphygmomanometry in detecting pulsus paradoxus because it results in a permanent recording of the arterial waveform and pressure and thus allows for an objective measurement. Due to its invasive nature, however, it is often painful to the patient and requires a highly trained health care provider.

Infrared photosensors used for pulse oximetry and plethysmography may be utilized for a third technique that may be used for detecting pulsus paradoxus. In this technique, changes in the intensity of an infrared (IR) beam passing through a patient's finger tip, toe, or earlobe are obtained to measure fluctuations in regional blood volume, a correlate of blood pressure. A clip-on probe sends an IR beam through the fleshy tissue and receives reflections therefrom. Changes in the amount of blood in the measurement area (i.e., a capillary bed) cause changes in absorption or variation, and such changes vary along with the amount of blood delivered to that tissue. Thus, although not a direct measure of the patient's blood pressure, the plethysmographic signal emulates the waveform contour and magnitude of direct intra-arterial pulse pressure and is typically displayed on a monitor screen along with the electrocardiogram and respiratory excursions. Clinical use of this measurement, called plethysmographic oximetry (PO), has been reported to detect pulsus paradoxus in children with pericardial tamponade and in adults with respiratory distress from obstructive lung disease but these results have not yet been incorporated into devices that would make possible simply applied, non-invasive, real-time detection of pulsus paradoxus.

The above described techniques for detection of pulsus paradoxus are highly subjective, labor intensive and inaccurate (if measured with a blood pressure cuff), or invasive (if done with arterial lines) and therefore, are rarely used. Thus, the ability to detect the ominous condition of pulsus paradoxus requires a high level of suspicion and cumbersome or invasive technology. As a result, pulsus paradoxus and therefore early signs of several life-threatening conditions often go undetected.

BRIEF DESCRIPTION OF THE DRAWINGS

The following illustration is by way of example and not by way of limitation in the figures of the accompanying drawings in which like references indicate like elements. It should be noted that references to "an" or "one" embodiment in this disclosure are not necessarily to the same embodiment, and such references mean at least one.

DETAILED DESCRIPTION

Automatic and sensitive detection of respiratory variation in cardiac activity may be a major asset in emergency departments, medical and surgical intensive care units (ICU), operating rooms, and hospices since it is especially difficult to determine worsening of many conditions with current manual systems and those focusing on changes in arterial blood pressure alone. Such detection may allow health care physicians to more quickly address and treat conditions such as, for example, chronic apnea and tension pneumothorax. Moreover, an automated system and method as described herein may be useful in nursing homes or hospices where detection of impending respiratory failure may allow families to be notified of important changes in conditions as they occur. Still further, detection of hemodynamic changes that happen consistently in obstructive sleep apnea may improve diagnosis or help avoid expensive diagnostic testing in sleep laboratories. It is thus believed, automated detection of pulsus paradoxus would help to identify and intervene in patient care resulting in thousands of lives saved each year.

In one embodiment, a method for detection of pulsus paradoxus is disclosed. In one aspect, the method includes detection of a pattern consistent with a respiratory cycle of waveforms representing cardiac oscillations to detect an abnormality in the pattern. In one embodiment, a plethysmographic oximeter system may be used to measure and display a respiratory waveform and concurrent waveform representing cardiac oscillations (plethysmograhic oximetry waveform) over a period of time. In this context, a lead from the system may include sensors for monitoring a patient's respiratory activity. The system may further include a lead for monitoring cardiac activities. Still further, leads may include electrocardiogram sensors (ECG) and/or sensors for detecting a pulse rate. The system may display information relating to each of these measurements in a waveform on an interface of the system. These waveforms may then be analyzed and scored by dividing averaged offsets of pulse waves from a base line with average wave amplitudes over a respiratory cycle. A score falling within a particular range indicates an abnormality (e.g. oscillating base of a plethysmographic wave from a baseline).

Figure 1A:
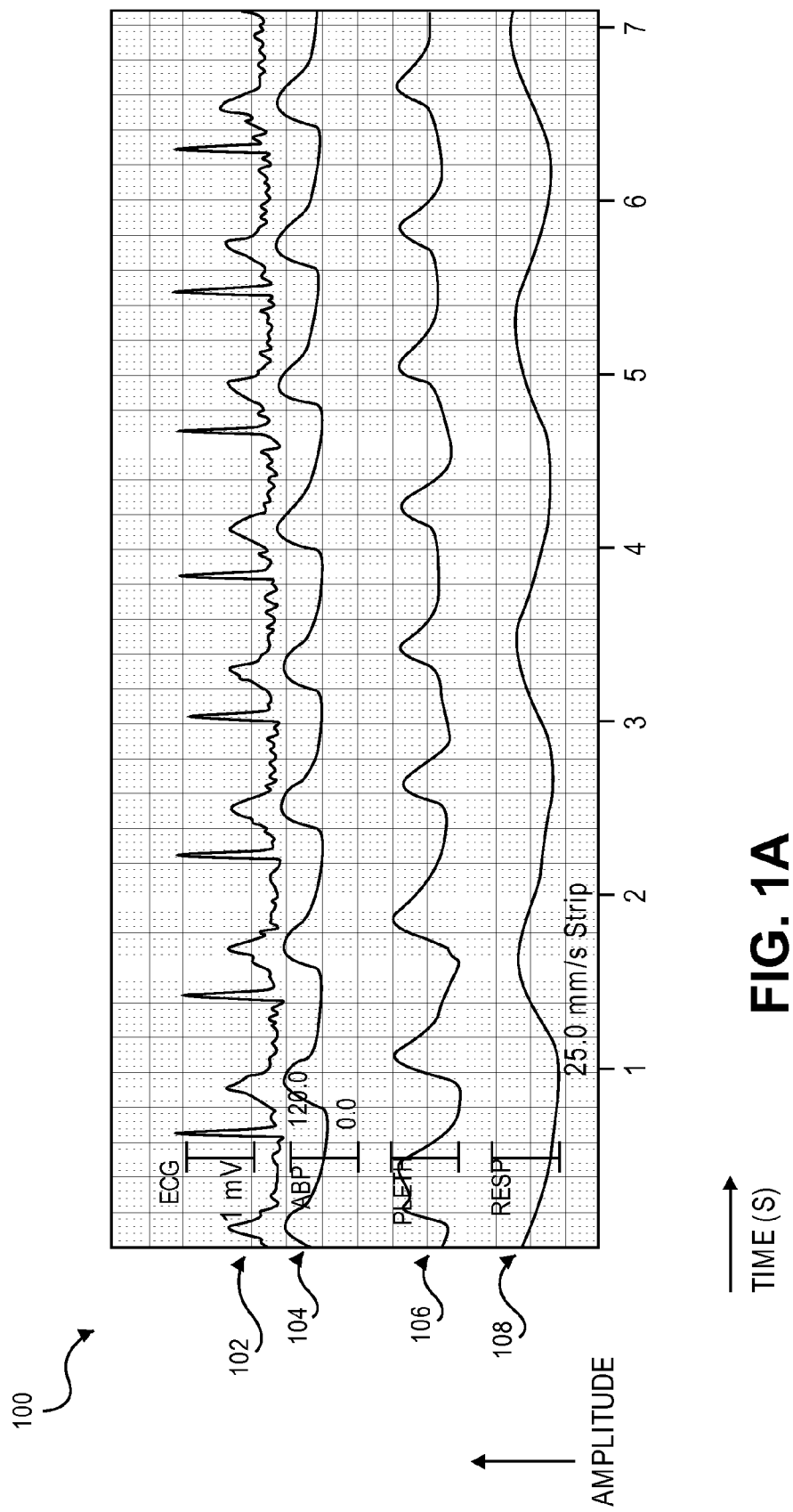
FIG. 1A illustrates simultaneous recordings from a patient of an electrocardiogram wave review (ECG), a blood pressure wave review (ABP), a plethysmographic wave review (PLETH) and a respiratory wave review (RESP).

FIG. 1A illustrates simultaneous normal ECG 102, ABP 104, PLETH 106 and RESP 108 recordings from a patient. ECG 102, ABP 104, PLETH 106 and RESP 108 include a tracing of consecutive cycles over a period of seven seconds. Components of the recordings illustrated in FIG. 1A will be described in more detail in reference to FIG. 1B.

An electrocardiogram (ECG) records electrical potentials from the heart. Under normal conditions, an electrical stimulus is generated by the sinus node located in the right atrium of the heart. The sinus node is the pacemaker of the heart and begins the process of depolarization of the atrium and ventricle through conduction pathways and generates an electrical stimulus which initiates the heart beat (e.g., 60 to 190 times per minute depending on the age of the patient). The electrical impulse travels from the sinus node to the atria ventricular (AV) node where it stops for a brief period and continues down the conduction pathways via the bundle of His into the ventricles. Accordingly, the right and left atria are depolarized first followed by depolarization of the right and left ventricle. As the electrical impulse moves through the conduction system, the heart contracts. Each contraction represents one heart beat.

Figure 1B:
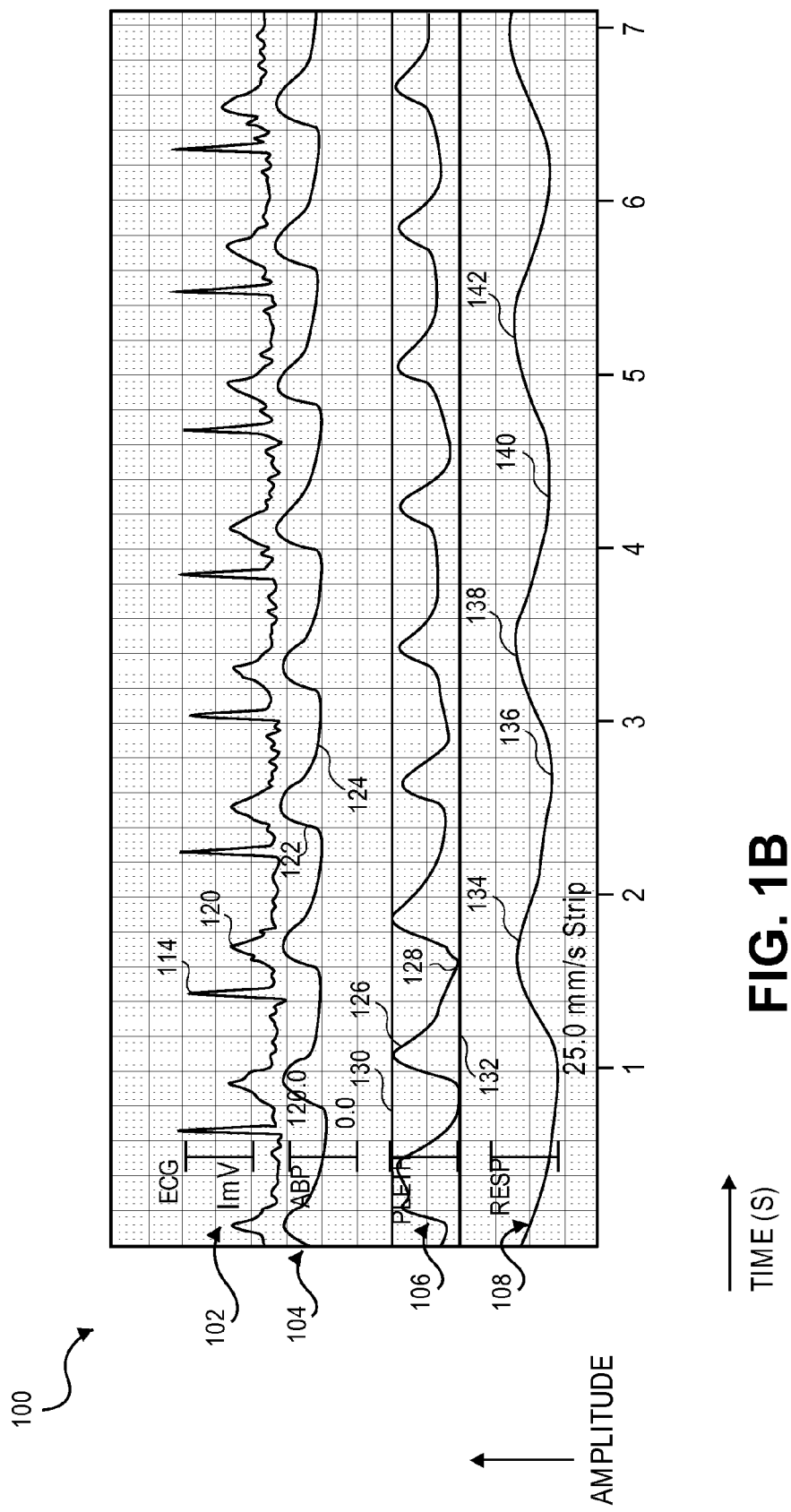
FIG. 1B illustrates the simultaneous recordings of FIG. 1A.

In FIG. 1B, the large vertical spike of ECG 102 is R wave 114 which represents depolarization of ventricles. Each R wave 114 is followed by contraction and pumping of blood. R wave 114 is used as a signal from which other signals are identified. The lower amplitude spike following R wave 114 is T wave 120. T wave 120 represents repolarization of cardiac muscle which then prepares for the next signal from the sinus node.

Each ventricular contraction produces an arterial waveform ABP 104 which can be seen to follow R wave 114 due to the time delay following depolarization and the time for blood to get to the peripheral recording site. ABP 104 is a recording of the arterial pressure. The recording utilizes a cannula inserted into an artery which is in turn transduced into a scaled electrical signal. The height or amplitude is scaled in mmHg. ABP 104 illustrates the ABP in the radial artery caused by the pressure generated by contraction of the heart's left ventricle. ABP includes a systolic pressure defined as the peak pressure in the arteries during the cardiac cycle and a diastolic pressure defined as the lowest pressure at the resting phase of the cardiac cycle. ABP waveform 104 includes "up" 122 and "down" 124 fluctuations of the arterial blood pressure resulting from the pulsatile nature of the cardiac output. The pulse pressure is determined by the interaction of the stroke volume versus the volume and elasticity of the major arteries. Normal ABP ranges for adult humans are systolic between 90 mmHg and 135 mmHg and diastolic between 50 mmHg and 90 mmHg.

Referring to PLETH wave review 106, the waveform represents a patient having a steady unchanging pulse with a heart rate of about 80 beats per minute. PLETH waveform 106 may be recorded from a fingertip device utilized to determine an index of tissue oxygenation. In this aspect, each wave represents a pressure exerted when the heart contracts. For a typical healthy adult human a normal PLETH waveform 106 is about 120 mmHg/60 mmHg. Horizontal borderlines 130, 132 are illustrated along waveform 106 to emphasize the regularity of the waves. In particular, peak borderline 130 extends along an upper limit defined by wave peaks 126 of PLETH waveform 106 and baseline 132 extends along a lower limit along wave bases 128 of PLETH waveform 106. It can be seen that the waves of PLETH waveform 106 have a regular height or amplitude (i.e., distance from peak 126 to baseline 132). In addition, each wave base 128 is substantially aligned with baseline 132 such that no significant baseline oscillations are present.

Referring to RESP wave review 108, the waveform represents respiratory excursions where "up" waves 134, 138, 142 represent inspiration and "down" waves 136, 140 represent expiration. RESP review 108 may be obtained from impedance plethysmography using standard ECG electrodes. Impedance plethysmography is a non-quantitative signal arising from movement of ECG sensors placed on the patient's thorax as the thorax rises and falls. RESP waveform 108 is shown having a regular respiratory tracing and may have a rate of approximately 16 to 30 breaths per minute. Wave peaks representing inspiration may be used to define each respiratory cycle. For example, a respiratory cycle may be defined by peaks 134 and 138 while another cycle may be defined by peaks 138 and 142.

It can be seen from FIGS. 1A and 1B that ECG 102, ABP 104 and PLETH 106 waveforms have the same frequency though it is noted that there is a physiologic offset such that the ABP signal occurs after ECG and the PLETH signal occurs after ABP. In a normal healthy human, there is a correlation in the ECG, ABP and PLETH waveforms and at most a subtle relationship between PLETH and RESP.

Figure 2:
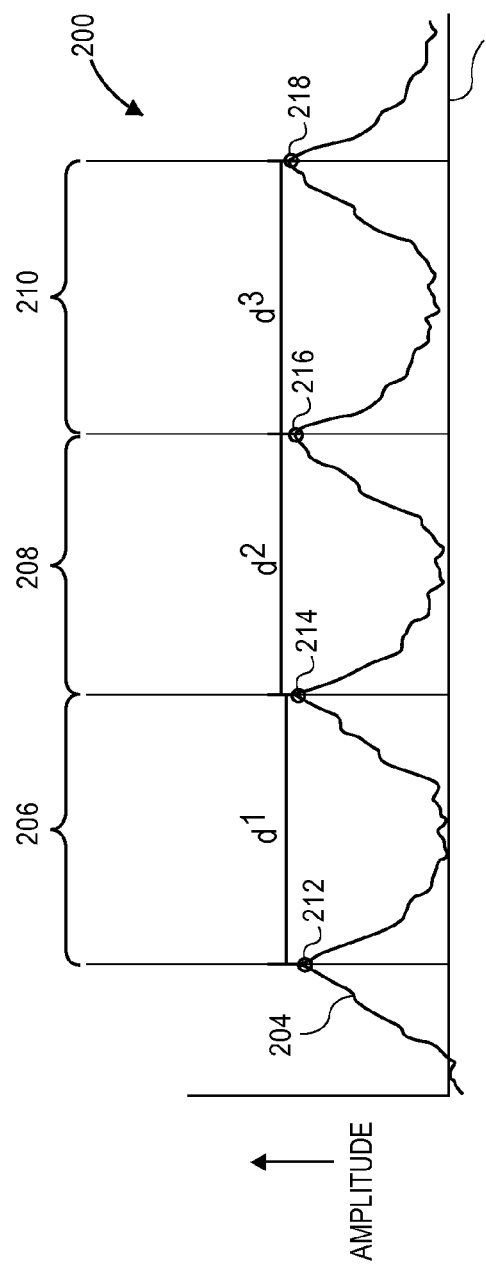
FIG. 2 illustrates a physiologic respiratory wave review of a patient.

FIG. 2 illustrates a physiologic respiratory wave review of a patient. RESP waveform 200 shows an exemplary embodiment of a physiologic wave review for purposes of illustrating a measurement of an average respiratory cycle distance for use in detection of an abnormality in a pattern representing cardiac oscillations. In this aspect, a waveform 204 of RESP 200 includes peaks 212, 214, 216, 218 representing inspiration. A baseline 202 from which an amplitude of peaks 212, 214, 216, 218 may be determined is further shown. An average respiratory cycle distance may be determined by first measuring a distance from one peak to the next. An average distance, D, may then be determined by averaging the distances of at least two consecutive respiratory cycles. For example, a distance, $d^1$, between peaks 212 and 214 may be measured to identify a first cycle 206 while a distance $d^2$ between peaks 214 and 216 may be measured to identify a second cycle 208. An average is taken of distance $d^1$ and $d^2$ to determine average respiratory cycle distance D. Still further, distance $d^3$ (between peaks 216 and 218) of a third respiratory cycle 210 may be measured and averaged with distances $d^1$ and $d^2$ to arrive at average respiratory cycle distance D.

Figure 3:
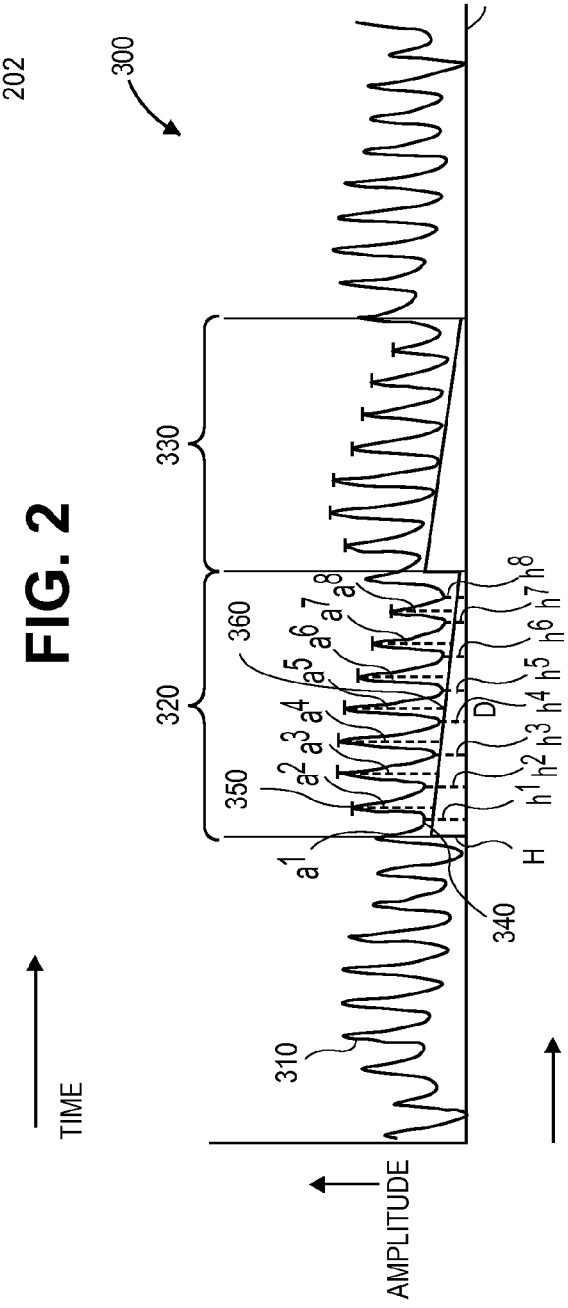
FIG. 3 illustrates a pathological wave review of a patient indicative of pulsus paradoxus.

FIG. 3 illustrates a wave review with variation in a PLETH waveform for a patient with a regular sinus rhythm. In particular, it can be seen from FIG. 3 that bases of waves of PLETH 300 are offset (i.e. oscillate) from a baseline 305. These oscillations may be analyzed to determine whether they are indicative of pulsus paradoxus by dividing the waves into groups, or cycles, which correspond to an average respiratory cycle distance, D, for the patient as described above. For the purpose of illustrating this concept, an average respiratory cycle D (e.g. average distance of cycles 206, 208, 210) as described above in reference to FIG. 2 is used to identify wave cycles 320, 330 of FIG. 3. It is recognized, however, that RESP waveform 200 and PLETH waveform 300 are not drawn to scale. For example, cycle 320 is identified by measuring average respiratory cycle D from the beginning of a blood pressure increase along baseline 305. Cycle 330 then extends a distance D from an end of cycle 320. It can be seen from FIG. 3 that each cycle 320, 330 includes about eight wave peaks 350 and thus approximately eight waves. Once a cycle is determined, a height, h, is measured from each wave base 340 to baseline 305. An average height, H, is then determined using each height, h, measured from wave bases 340 to baseline 305. For example, in cycle 320 an average height H may be calculated by adding each of heights $h^1$, $h^2$, $h^3$, $h^4$, $h^5$, $h^6$, $h^7$, $h^8$ together and dividing by eight. Average height H is then used to form a triangle as shown in FIG. 3 having a height H, a base D and hypotenuse 360 representative of a best-fit line to wave bases 340. An average wave amplitude, A, may then be determined for each cycle 320, 330 by determining an amplitude, a, of each wave from hypotenuse 360 to a wave peak 350 and averaging the amplitudes. For example, in cycle 320 an average amplitude A may be calculated by adding each amplitude $a^1$, $a^2$, $a^3$, $a^4$, $a^5$, $a^6$, $a^7$, $a^8$ from hypotenuse 360 to a wave peak 350 and averaging the amplitudes. The above described analysis may be repeated for cycle 330. A value (i.e., score) for cycles 320 and 330 may then be determined according to the formula H/A wherein H represents the average offset from the baseline of the waves and A represents average amplitude for cycle. Using the above analysis, the degree of wave oscillations within each cycle may be evaluated to determine whether they are indicative of pulsus paradoxus.

For example, in one embodiment illustrated in FIG. 3, average distance, D, may be approximately 3.5 centimeters (cm) such that cycle 320 is made up of waves within a region of baseline 305 3.5 cm in length. An average height, H, of cycle 320 may be approximately 0.356 cm (i.e., $h^1$=0.5 cm, $h^2$=0.5 cm, $h^3$=0.4 cm, $h^4$=0.3 cm, $h^5$=0.3 cm, $h^6$=0.3 cm, $h^7$=0.25 cm, $h^8$=0.3 cm) and average amplitude A may be approximately 1.113 cm (i.e., $a^1$=0.7 cm, $a^2$=1.1 cm, $a^3$=1.3 cm, $a^4$=1.35 cm, $a^5$=1.25 cm, $a^6$=1.2 cm, $a^7$=1.1 cm, $a^8$=0.9 cm) resulting in a score of 0.32 (0.356 cm/1.113 cm). In one embodiment, an alarm 560 (See FIG. 5) may be triggered by a score (calculated, for example, as described above, offset over amplitude) falling within a range indicative of pulsus paradoxus (i.e., pressure decrease greater than 10 mmHg). Thus, in one embodiment a value indicative of pulsus paradoxus may be 0.32. In one aspect, a range indicative of pulsus paradoxus may be, for example, a score from about 0.3 to about 2.5 and still further a score from about 1.6 to about 2.5 may be indicative of pulsus paradoxus. It is believed a score below 0.3 is within the normal range. Still further, alarm 560 may be triggered by a score indicative of a variety of cardiopulmonary disorders, often in combination. In this aspect, the alarm may be triggered by a score in a range of, for example, about 0.3 to about 1.6.

As described herein, variations in a plethysmographic signal as previously described may indicate pulsus paradoxus. It is further contemplated, however, that each of the wave reviews illustrated in FIGS. 1A and 1B (ECG, ABP, RESP), should be considered in determining whether or not variations in a patient's plethysmographic signal are indicative of pulsus paradoxus or some other condition. For example, where plethysmographic signal variations are detected in a patient with an irregular sinus rhythm, the variations in the plethysmographic signal may correspond to the irregular sinus rhythm thereby suggesting an arrhythmic, rather than respiratory related, reason for the variations.

Figure 4:
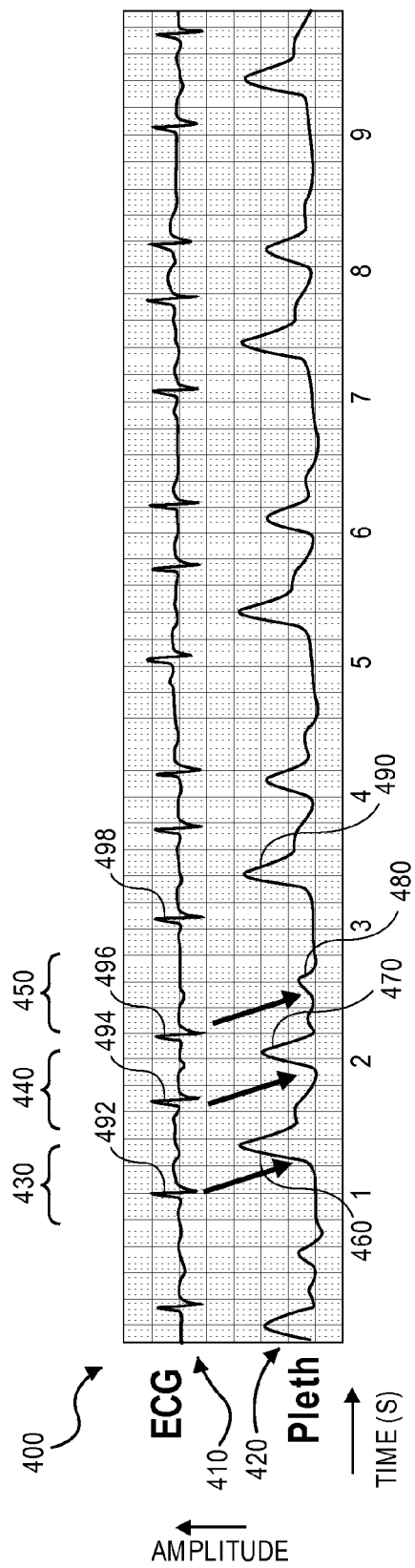
FIG. 4 illustrates a pathological wave review of a patient indicative of changes in stroke volume resulting from premature atrial beats.

FIG. 4 illustrates one such pathological wave review of a patient indicative of changes in stroke volume resulting from premature atrial beats. The term "stroke volume" as used herein refers to the volume of blood ejected from a ventricle with each beat of the heart. FIG. 4 shows wave review 400 including an ECG waveform 410 and PLETH waveform 420 of a patient. In this embodiment, an abnormality is detected based upon the frequency of ECG 410 complexes with respect to PLETH 420 over several consecutive cycles 430, 440, 450. In particular, in review 400, PLETH 420 illustrates three repetitive plethysmographic waves 460, 470, 480 corresponding to cycles 430, 440 and 450 of ECG waveform 410. Waves 460, 470, 480 represent a late beat 460 following a pause, a normal beat 470 and a premature beat 480. In particular, beat 460 is seen having a large amplitude due to the extra fill time resulting from a pause preceeding the beat. In the case of premature beat 480, the resulting pulse has a much lower amplitude than normal because the heart does not have an adequate fill time. This pattern of late, normal and premature beats then continues such that the next beat 490 following beat 480 has an adequate fill time and thus appears much like beat 460. The magnitude of these waves matches the expected variation in stroke volume illustrated by ECG R waves 492, 494, 496, 498. Accordingly, upon viewing this pattern, a health care provider will recognize that the variability in PLETH 420 corresponds to the pattern of heart beats shown in ECG 410 and should therefore dismiss concerns regarding pulsus paradoxus.

Figure 5:
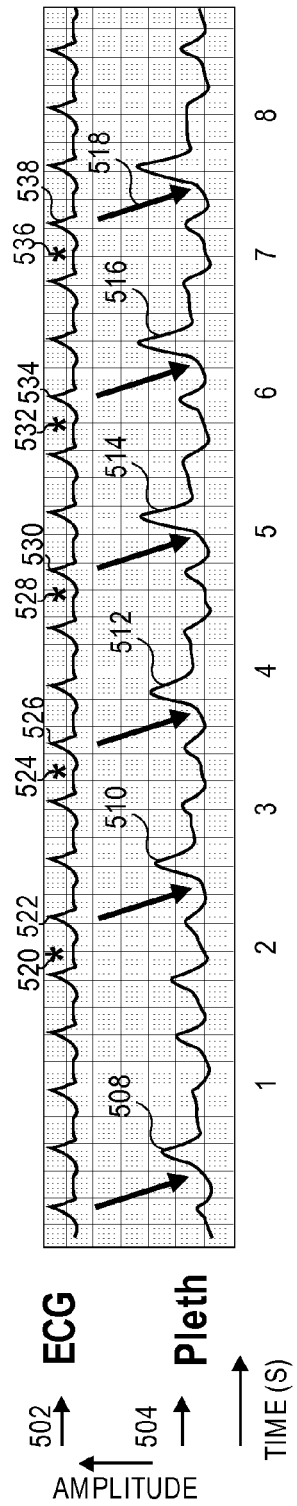
FIG. 5 illustrates a pathological wave review of the patent of FIG. 4 indicative of wide complex tachycardia.

FIG. 5 illustrates a wave review comparison of an ECG waveform and PLETH waveform of the patient from FIG. 4. Wave review 500 shows ECG 502 and PLETH 504 waveforms. ECG 502 demonstrates a wide complex tachycardia, rate 140, without obvious P waves. P waves represent depolarization of the atria. PLETH 504 depicts periodic large pulses 508, 510, 512, 514, 516, 518 resulting from intermittent sequential atrio-ventricular contractions, diagnostic of ventricular contractions with atrio-ventricular dissociation. The slower atrial rhythm is not obvious on ECG 502 but the presence of P waves can be discerned by subtle flattening of T waves 520, 524, 528, 532, 536 preceding each of the R waves 522, 526, 530, 534, 538, respectively, responsible for the larger plethysmographic excursions (pulses) 508, 510, 512, 514, 516, 518 of PLETH 504. In this aspect, a health care provide viewing these results can see that the variability in PLETH 504 corresponds to the pattern of heart beats depicted by ECG 502 and therefore the variability is heart beat by heart beat rather than respiratory thus eliminating pulsus paradoxus as a potential cause of the variability.

It is further appreciated that Traube-Hering-Mayer waves may further be responsible for variations in a plethysmographic waveform. Traube-Hering-Mayer waves are oscillations that have been measured in association with blood pressure, heart rate, cardiac contractility, pulmonary blood flow, cerebral blood flow and movement of the cerebrospinal fluid, and peripheral blood flow including venous volume and thermal regulation. The waves exhibit a rate typically slightly less than and independent of respiration and resemble the primary respiratory mechanism. Thus, where, for example, a fluctuation in pulse pressure with the frequency of respiration persists after respiration has been arrested, Traube-Hering-Mayer waves, in addition to respiratory causes, should be considered in evaluating the cause of the fluctuation.

Figure 6:
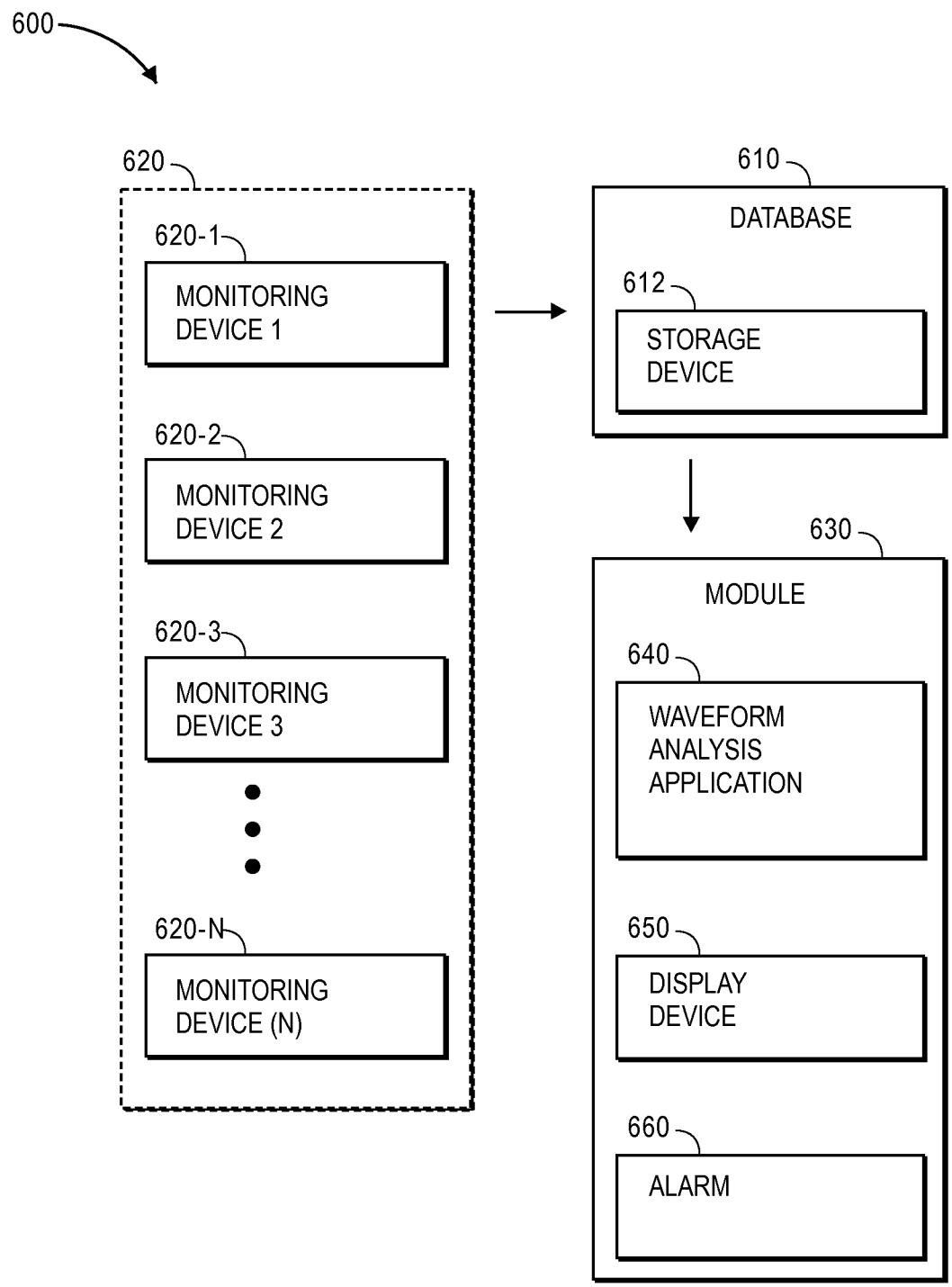
FIG. 6 illustrates a system for detecting pulsus paradoxus.

FIG. 6 illustrates a system 600 detecting waveform patterns and detecting an abnormality in the pattern. In this aspect, system 600 includes a database 610 to receive and store data representing a physiological condition of the patient over a period of time, wherein the data comprises data corresponding to respiratory activity and cardiac oscillations. The data corresponding to the respiratory activity and cardiac oscillations may be recorded and stored in a storage device 612 of database 610. System 600 may include a patient monitoring device 620 to generate data representing a physiological condition of a patient over time for storage in database 610. In an alternative embodiment, system 600 may include any number of patient monitoring devices 620 connected to a patient to measure, for example, heart rate, blood volume, systolic and diastolic blood pressure, and/or plethysmographic oxygen saturation. In this aspect, patient monitoring devices 620 include, monitoring devices 620-1 through 620-N. In one embodiment, patient monitoring device 620 may be a plethysmographic oximeter or any similar device capable of measuring and displaying respiratory and/or cardiac activity. In an alternative embodiment, patient monitoring device 620 may include a plethysmographic oximeter and an ECG (e.g., monitoring device (620-1) is a plethysmographic oximeter and monitoring device (620-2) is an ECG). Data generated by patient monitoring devices 620 may be in various formats. In one embodiment, the data may be in text format. In an alternative embodiment, the data may be in a waveform format suitable for providing a waveform image.

System 600 may include module 630 to receive and process data generated by monitoring devices 620. In this aspect, module 630 may include a waveform analysis application 640 running on module 630. In one embodiment, waveform analysis application 640 converts waveform data into a quantifiable format for measuring changes in waveform characteristics. In this aspect, portions of the waveform data are examined by waveform analysis application 640 to extract features or patterns that are pertinent to analysis of the waveform data. There are a number of techniques that may be used to extract pertinent information from the waveform data. For example, pertinent information from the waveform data can be extracted by determining frequency and amplitude of the waveforms at various points. The waveform data can also be analyzed by examining at least two cycles of the waveform in conjunction with a second waveform. This may be accomplished by capturing a segment of the waveform data of each waveform and defining a single cycle and analyzing the captured segment perhaps by applying a suitable algorithm, such as pattern recognition algorithm or transform algorithm. For example, waveform analysis application 640 may be configured to extract a pattern consistent with a respiratory cycle of a waveform representing cardiac oscillations illustrated in FIG. 3 by examining relevant data according to the above processes.

In one embodiment, waveform analysis application 640 may further be configured to monitor the waveform patterns and extract abnormal patterns (e.g. wave oscillations in cardiac waveforms) as described in reference to FIG. 3. When an abnormality in, for example, a plethysmogrhpic waveform is found for several consecutive respiratory cycles, storage of the two signals (respiratory and cardiac) is begun. The signals are then quantified and compared to determine a score as previously discussed. If the score is within a range indicative of an abnormality such as pulsus paradoxus, alarm 660 further included in module 630 sounds alerting the care provider. Alternatively or in addition to, information pertinent to the waveform data may be extracted manually. This may be accomplished by, for example, a person who is trained to recognize pulsus paradoxus by manually examining the physiological data (including waveform data) displayed on a display device 650 (i.e. interface) of module 630.

In the preceding detailed description, specific embodiments are described. It will, however, be evident that various modifications and changes may be made thereto without departing from the broader spirit and scope of the claims. The specification and drawings are, accordingly, is to be regarded in an illustrative rather than restrictive sense.

What is claimed is:

1. A system comprising:
   a database to store data representing a physiological condition of a patient over a period of time, wherein the data comprises data corresponding to respiratory activity and data corresponding to cardiac oscillations, wherein the data corresponding to respiratory activity comprises a first waveform and the data corresponding to the cardiac oscillations comprises a second waveform; and
   a module for detecting a pattern of the second waveform consistent with a cycle of the first waveform and detecting an abnormality indicative of pulsus paradoxus in the pattern, and
   wherein detecting the abnormality comprises determining a value from the pattern based on an average offset of wave bases of the second waveform from a baseline and an average amplitude of wave peaks of the second waveform from a best-fit line to the wave bases.

2. The system of claim 1, wherein the second waveform comprises a plethysmographic waveform and the first waveform comprises a respiratory waveform.

3. The system of claim 1, further comprising:
an interface for displaying the first waveform and the second waveform.

4. The system of claim 1, wherein each of the first waveform and the second waveform data is generated by a pulse oximeter.

5. The system of claim 1, wherein the first waveform data and the second waveform data is generated from a plurality of monitoring devices coupled to a patient.

6. The system of claim 1, wherein the second first waveform data comprises an electrocardiogram (ECG) waveform.

7. The system of claim 1, wherein the waveform representing respiratory activity is obtained from impedance plethysmography using an electrocardiogram (ECG) coupled to a patient.

8. The system of claim 1, wherein when the abnormality is detected an alarm is triggered to alert a health care provider of the abnormality.

\* \* \* \* \*